United States Patent [19]

Bond et al.

[11] 4,109,643
[45] Aug. 29, 1978

[54] PERFUSION METER

[75] Inventors: Albert K. Bond, Burlington; Edwin B. Merrick, Stow; Larry Lee Nielsen, Burlington, all of Mass.

[73] Assignee: Hewlett-Packard Company, Palo Alto, Calif.

[21] Appl. No.: 696,973

[22] Filed: Jun. 17, 1976

[51] Int. Cl.² .............................................. A61B 5/02
[52] U.S. Cl. ................ 128/2 L; 128/2.05 P; 356/41
[58] Field of Search ......... 128/2 G, 2 H, 2 L, 2.05 F, 128/2.05 P, 2.05 V, DIG. 29; 356/40–41

[56] References Cited

U.S. PATENT DOCUMENTS

| 3,152,587 | 10/1964 | Ullrich et al. | 128/2 L |
|---|---|---|---|
| 3,403,555 | 10/1968 | Versaci et al. | 128/2.05 F X |
| 3,628,525 | 12/1971 | Polanyi | 128/2 L |
| 3,638,640 | 2/1972 | Shaw | 356/41 X |
| 3,677,648 | 7/1972 | Dorsch | 128/2.05 F UX |
| 3,704,706 | 12/1972 | Herczfeld et al. | 128/2.05 P |
| 3,796,213 | 3/1974 | Stephens | 128/2.05 P |
| 3,841,314 | 10/1974 | Page | 128/2 L |
| 3,970,074 | 7/1976 | Mogos et al. | 128/2 H |
| 3,980,075 | 9/1976 | Heule | 128/2.05 P |
| 3,998,550 | 12/1976 | Konishi et al. | 356/39 |
| 4,001,667 | 1/1977 | Bober | 356/41 X |
| 4,003,370 | 1/1977 | Emil et al. | 128/2.05 D |

Primary Examiner—Robert W. Michell
Assistant Examiner—Francis J. Jaworski
Attorney, Agent, or Firm—David A. Boone

[57] ABSTRACT

A perfusion meter comprising a hand-held battery operated optical plethysmograph displays an indication of blood flow rate in response to the time-varying optical transmission characteristics of an ear or other organ. This indication, called the perfusion index, is proportional to both the amplitude and frequency of variations in the dynamic optical transmission characteristics of the ear or other organ.

3 Claims, 15 Drawing Figures

PERFUSION METER

BACKGROUND AND SUMMARY OF THE INVENTION

In general, previous instruments utilizing photoelectric techniques have been limited to monitoring blood flow and have not provided accurate blood flow rate measurements. Some of these previous techniques for blood flow rate monitoring have used a plethysmograph to monitor blood flow through an organ, typically the pinna of an ear or one of the patient's fingers. See, for example, an article in the American Journal of Physiology, 1940, Volume 130, No. 1 by Alrick B. Hertzman and John B. Dillon, entitled "Distinction Between Arterial, Venous and Flow Components in Photoelectric Plethysmography in Man." Also see, for example, U.S. Pat. No. 3,796,213 issued to Frederick Richard Neason Stephens on Mar. 12, 1974 and entitled, "Perfusion Monitor."

Photoelectric techniques for monitoring or measuring blood perfusion are based on the phenomena that changing blood volume gives rise to a changing light absorption and hence changes in the amplitude of a signal produced by a photosensitive device. Photoelectric plethysmographs are used extensively for studying relative changes in skin blood flow and and as a transducer for heartrate monitors. However, problems associated with calibration, linearity, and stability, have all but eliminated the use of photoelectric plethysmography for accurate non-invasive blood flow measurement.

Also, oximeters have been used to measure the quantity of oxygen in a patient's blood. However, in many instances the usefulness of the oximeter has been limited because certain patients, e.g., those in post-surgical recovery, have sufficient peripheral vaso-constriction to limit the application of the oximeter. This is because while the oximeter can indicate when the quantity of blood in a tissue being measured is sufficient it cannot give an indication of its flow state. Consequently, because of the insufficient blood flow, the oximeter typically analyzes a mixture of venous and arterial blood and thus gives an $A_{os}$ measurement of smaller value than it should be. It is therefore necessary to accurately measure the blood flow rate through the tissue to calibrate the oximeter readings, but, as stated above, prior art perfusion meters have not provided the desired accuracy and convenience. Hence, to determine the flow rate of blood within a tissue area under test and to provide a method for estimating the accuracy of an oximeter reading, the perfusion meter in accordance with the present invention has been developed.

The physiological parameter that makes possible all photoelectric plethysmographic techniques is the pulsatile color changes associated with blood flow through the microcirculatory vessels. As mentioned above, photoelectric plethysmographic techniques have been used for studying relative changes in skin blood flow but many problems are encountered when attempts are made to make accurate perfusion measurements. For example, a primary cause of linearity problems is the response characteristics of the photosensitive device used in the plethysmograph.

Figure 1:
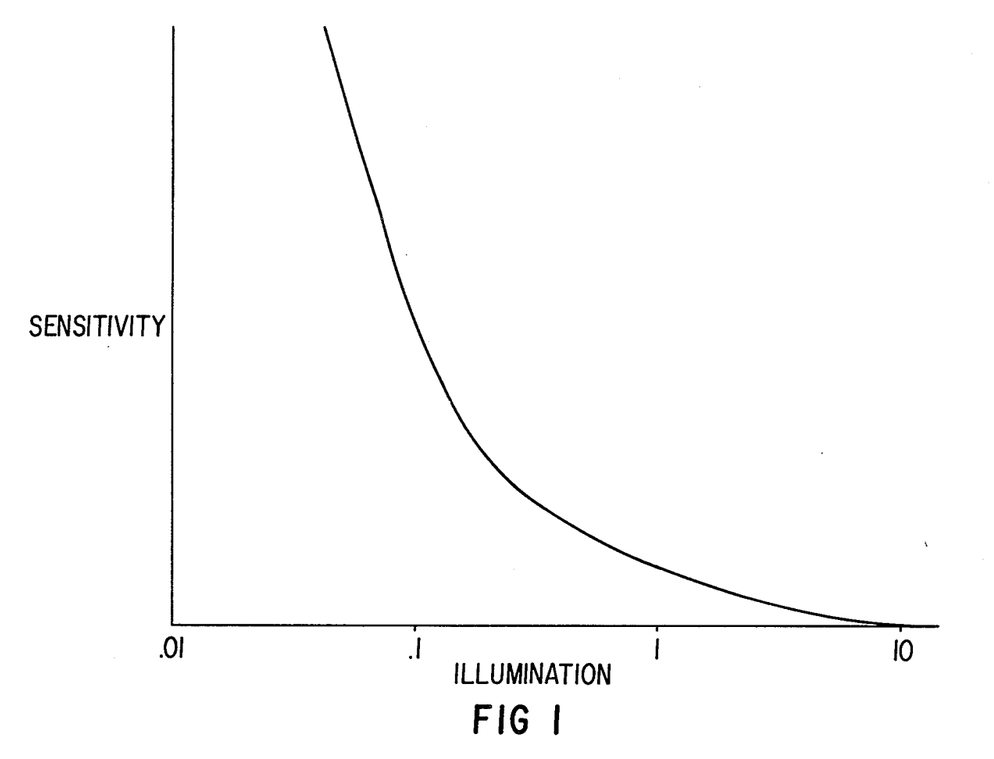
FIG. 1 is a graph showing the characteristic response of a typical photosensitive device to illumination.

All known photosensitive devices, with the exception of a photodiode which has a low level output, have non-linear response characteristics similar to that shown in FIG. 1. Also photosensitive devices have some variation with parameters other than light but in general, the more sensitive the device the worse the stability problem. For example, photoconductive cells typically suffer from large variations with temperature and light history problems so that their usefulness has definitely been limited, at least as it applies to accurate blood flow rate measurement. Phototransistors, while being fairly stable, suffer from non-linearity problems as well as being susceptible to radio frequency interference because of their rectifying junctions. Hence, even with calibration, which was only temporary at the best, prior art photoelectric plethysmographic techniques (transmissive and reflective) could not reliably be used for accurate non-invasive blood flow rate measurement.

In accordance with the preferred embodiment of the present invention, a light emissive device provides illumination through body tissue to a photosensitive device. A signal is produced which represents the log of the transmitted light. Changes in the log of the signal produced in response to the transmitted light are utilized to produce indications representing changes in the pulsatile blood flow rate.

DESCRIPTION OF THE PREFERRED EMBODIMENT

It is in the capillaries that the most purposeful function of circulation occurs, namely the interchange of nutrients and cellular excreta between the tissues and the circulating blood. To accomplish this, an estimated 3,600,000,000 capillaries are distributed throughout the human body so that they are rarely more than 20 microns away from a single functional cell.

Figure 2:
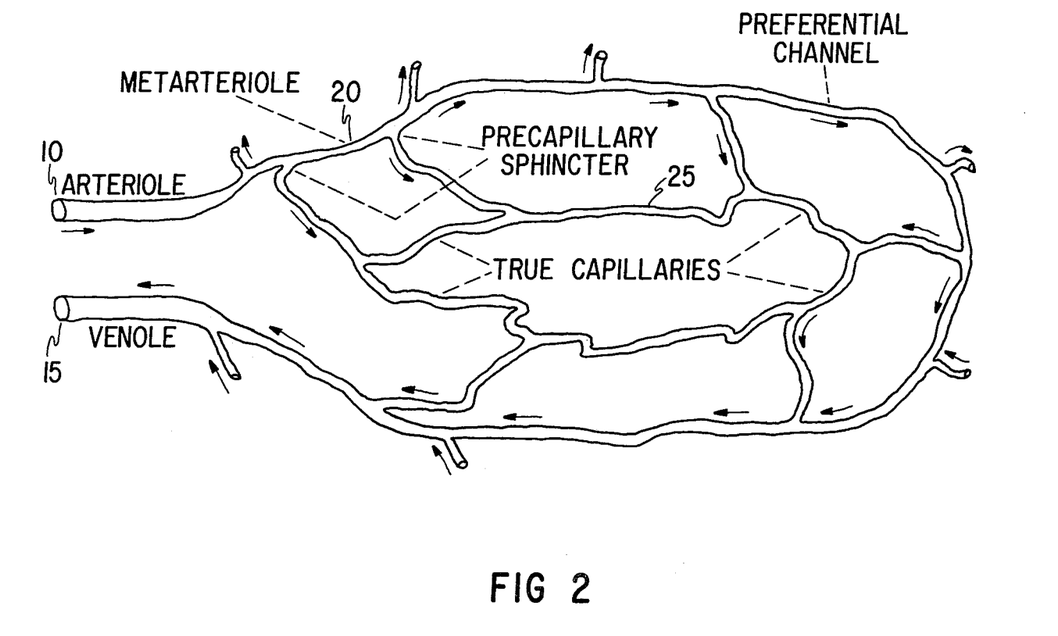
FIG. 2 illustrates the structure of a typical capillary bed.

FIG. 2 illustrates the structure of a "unit" capillary bed and shows the arterial blood entering via an arteriole 10 passing through a capillary bed and leaving by way of a venule 15. Blood from the arteriole 10 passes into a series of meta-arterioles 20 and from there into capillaries 25. Some capillaries are relatively large and are called the preferential channels, while the smaller capillaries are sometimes referred to as true capillaries. After passing through the capillaries or through an A-V shunt, the blood passed through a venule and then into the veins. The veins are capable of constricting and enlarging and thus they can store or pump the blood back into general circulation.

The arterioles 10 are highly muscular and can change their diameters many times. The meta-arterioles 20 do not have a continuous muscular wall, but smooth muscle fibers encircle the vessels at intermediate points. Smooth muscle fibers, called the precapillary sphincters, usually encircle the capillaries at their inlet. The venules 15 are considerably larger than arterioles 10 and have a much weaker muscular coat.

Vasomotion, i.e., the intermittant or discontinuous flow of blood through the capillaries, is caused by the intermittent contraction and relaxation of the meta-arterioles and precapillary sphincters. Vasomotion regulation is primarily a function of the concentration of oxygen in the tissues. Typically, only 10–15% of the tissue capillaries are open.

Despite the fact that blood flow through each capillary is intermittant, there are so many capillaries in a given area of body tissue that their overall function becomes averaged, i.e., there is an average rate of blood flow through each tissue capillary bed. Likewise, the tissue perfusion measured by the preferred embodiment is the average blood flow through the unit tissue area.

Although each capillary has a minute cross-sectional area, there are so many capillaries in the circulatory system that the total cross-sectional area is very large. Since the velocity of blood flow varies inversely with the cross-sectional area, it can readily be appreciated why the blood flows so slowly in the capillaries. This combination, blood velocity and blood crosssectional area, gives vascular color to the skin. The hue is determined by the rate at which the blood flows through the capillaries, while the intensity of the color is determined by the thickness of the blood layer. Hence, both the diameter of the microcirculatory vessels and the number of conducting vessels influence color brilliance, and the transmissivity of a given tissue area.

These pulsatile color changes associated with blood flow through the microcirculatory vessels are the physiological parameter upon which all photoelectric plethysmographic techniques are based. As stated above, photoelectric plethysmographs have been used for studying relative changes in skin blood flow, but their linearity, stability, and calibration problems have all but eliminated their use for non-invasive perfusion measurements. However, using the techniques of the preferred embodiment, accurate non-invasive blood flow rate measurement is now possible.

The perfusion meter of the preferred embodiment is a single-wave length device based on a Beer's law model of the optically absorbing material in the ear or other tissue. In this model, it is assumed that, in the absence of any field motion, the only short-term change in the absorbent spectrum is due to the pulsatile color changes associated with blood flow through the microcirculatory vessels.

To understand this model, consider a single light absorber of thickness $d$ concentration $c$ which receives light $I_o$ and transmits light $I$. The transmittance of the light absorbing substance at wave length $\lambda$ is given by $$T(\lambda) = I/I_o = e^{-E(\lambda)cd} = E^{-A(\lambda)}$$

and the absorbance $A(\lambda)$, of the substance at wave length $\lambda$ is given by $$A(\lambda) = -\ln(I/I_o) = E(\lambda)cd$$

In both of the above equations, $E(\lambda)$, is a proportionality constant known as the molar extinction coefficient which varies as a function of the material and wave length of light.

Note that if a mixture of two or more substances, e.g., a first substance having a concentration $C_1$ and a thickness $D_1$, a second substance having a concentration $C_2$ and a thickness $D_2$, . . . , and an Nth substance having a concentration $C_N$ and a thickness $D_N$, are contained in one sample, the absorbances of each will be added as follows:

$$A(\lambda) = -\ln(I/I_o) = E_1(\lambda)C_1d_1 + E_2(\lambda)C_2d_2 + \ldots + E_N(\lambda)C_Nd_N$$

If this happens to be a tissue sample with pulsatile blood flow, one of the above absorbent spectra, ($HbO_2$ + $Hb$), will be changing with time, while in the absence of field motion, all others should remain very nearly constant. Thus, by taking the derivative of the above equation with respect to time, the following is obtained:

$$\frac{d}{dt} A(\ ) = -\frac{d}{dt} \ln(I/I_o) = \frac{d}{dt} E_1(\lambda)C_1d_1 + \frac{d}{dt} E_2(\lambda)C_2d_2 + \ldots + \frac{d}{dt} E_N(\lambda)C_Nd_N$$

Furthermore, to relate linearity to pulsatile blood flow the following mathematical manipulation can be done.

$$\Delta \ln(I/I_o) = \Delta \ln I - \Delta \ln I_o = -\Delta E_b(\lambda)C_b d_b$$

$$\Delta \ln I = -\Delta E_b(\lambda)C_b d_b$$

This resulting equation, a time-varying log function, indicates that all fixed absorbers and system gain factors can be ignored and that in the absence of field motion, the changes in the log of the transmitted light are directly proportional to the changes in the blood thickness — concentration product, that is, the changing blood volume in the field of view.

Figure 10:
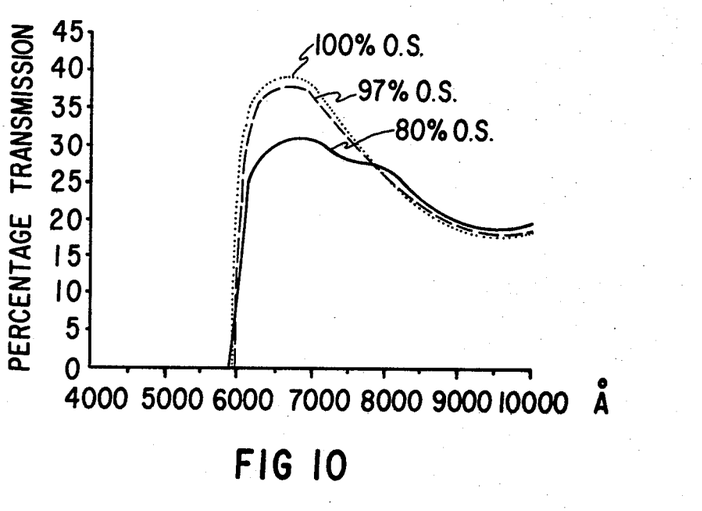
FIG. 10 is a graph showing the absorption spectra of blood through a typical ear at different oxygen concentrations.

Deoxyhemoglobin and oxyhemoglobin are the main absorbers of the blood and they have different absorption spectra, as is illustrated in FIG. 10. Choosing a wavelength between 6200Å and 8000Å gives greater sensitivity to oxyhemoglobin while a wavelength between 8000Å and 10000Å gives slightly greater sensitivity to deoxyhemoglobin. The ideal wavelength is approximately 8000Å for there both deoxyhemoglobin and oxyhemoglobin have the same absorption. Unfortunately, neither a source nor a detector is commercially available at 8000Å so a compromise solution must be chosen.

Figure 9:
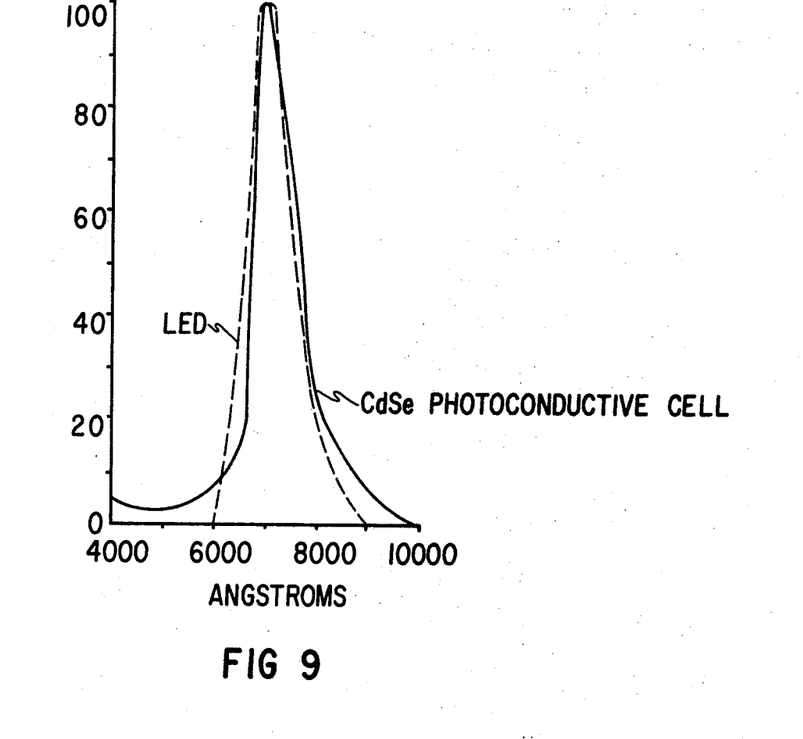
FIG. 9 shows the matching of the light emissive device and the photoconductive device of the preferred embodiment.

It is desirable to match the spectral response of the light emissive device to the photodetecting device to minimize ambient light interference and system power requirements. The former of these is important in order to give the best possible signal to noise ratio. The latter is particularly important if the system is battery operated. FIG. 9 shows that with proper selection of a CdSe photoconductive cell and a GaP red solid state lamp or light emitting diode (LED) an extremely well matched spectral response may be obtained. The combination of these two devices yields a sevenfold improvement in current drain over that obtained with the use of an incandescent lamp. Additionally, the LED provides for a safer (less heat) system as well as for greater reliability. As for speed of response, the selected CdSe photoconductive cell is fast enough to handle the relatively slow cardiac pulse activity.

With this selection complete, it is now essential that the historical problems associated with calibration, linearity and stability be eliminated. This is accomplished by using standard components having a sensitivity response as shown in FIG. 1, and coupling them with an element having a logarithmic response. Any non-linearity in a resistance-illumination curve is acceptable as long as it approximates a straight line when plotted on log-log paper.

Figure 11:
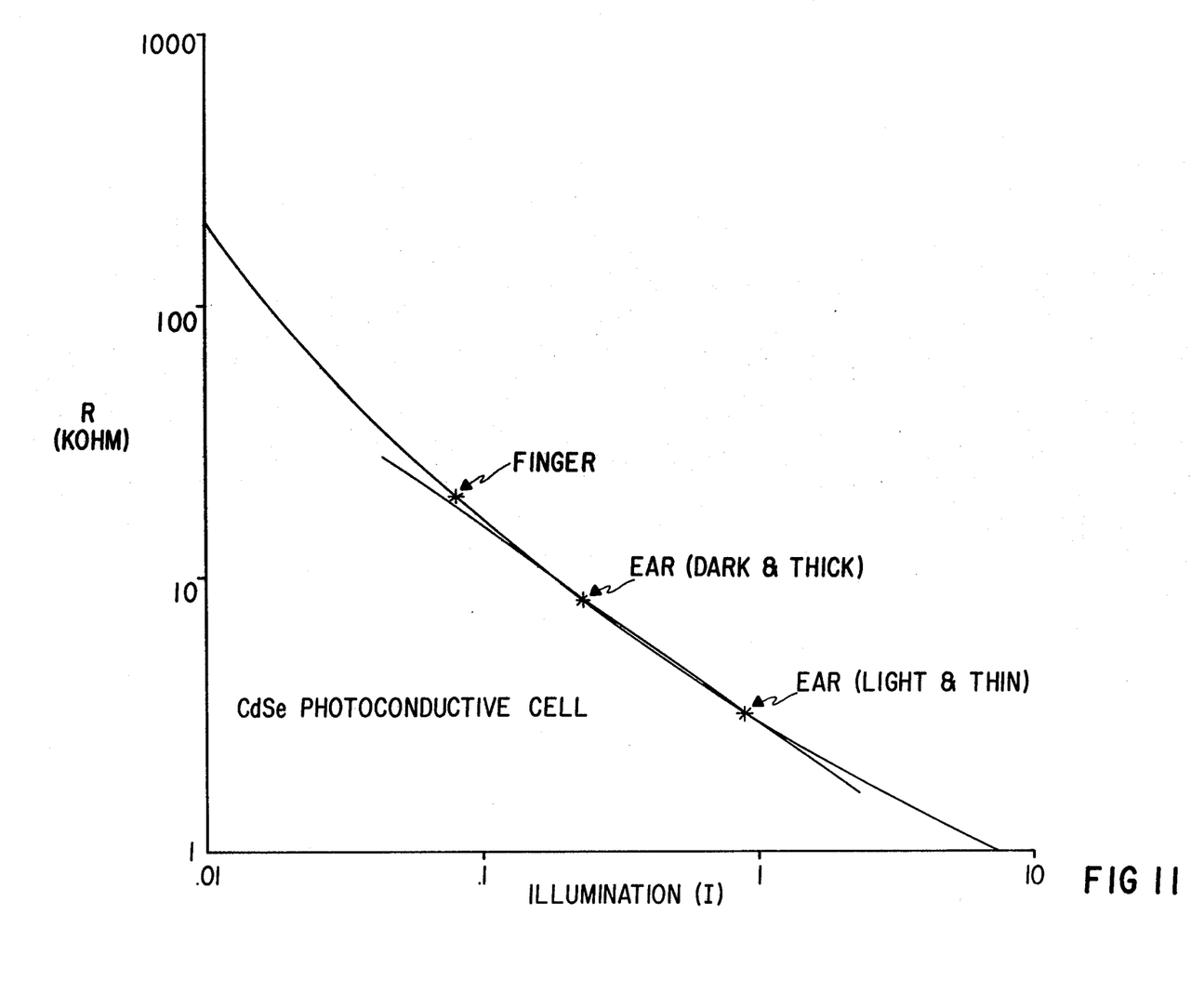
FIG. 11 is a graph of the response of the preferred embodiment to varying tissue samples.

A graph of responses obtained using the preferred embodiment is shown in FIG. 11.

Figure 6A:
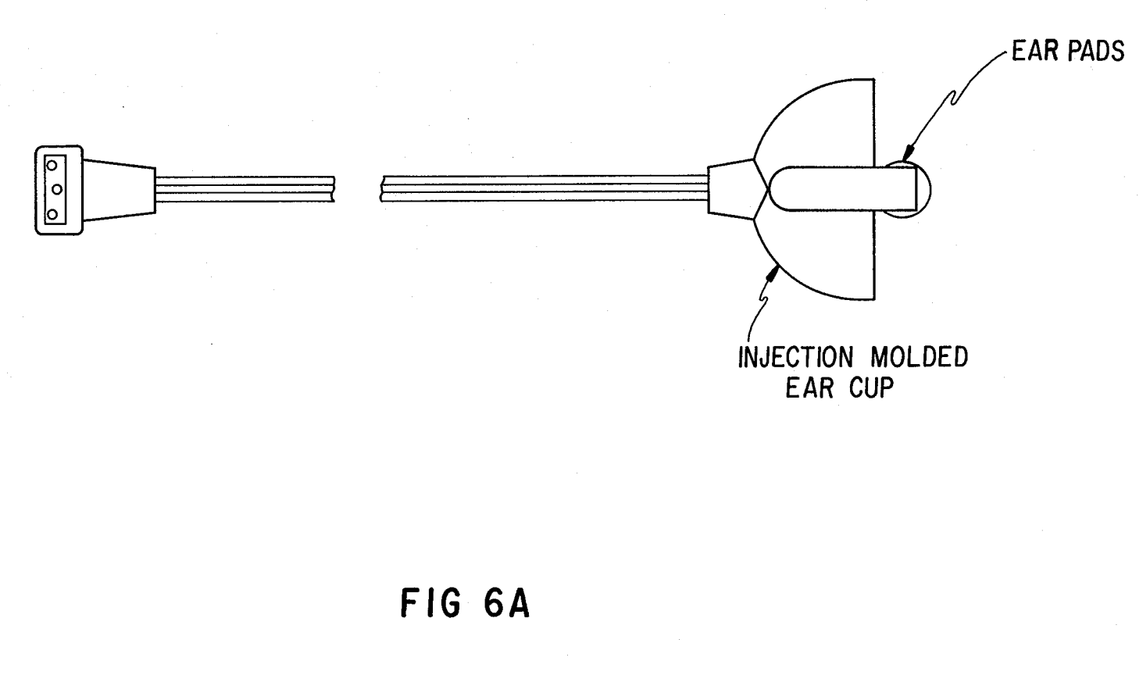
FIGS. 6A, 6B, 6C and 6D comprise an illustration of the optical plethysmograph of the present invention.
Figure 6B:
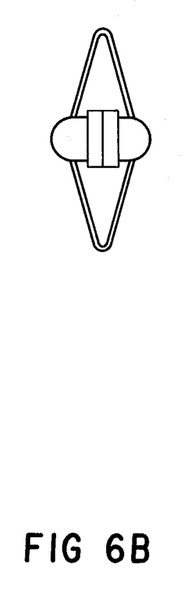
Figure 6C:
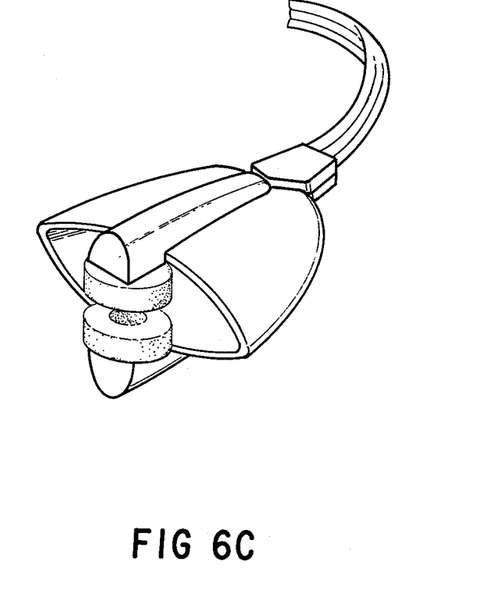
Figure 6D:
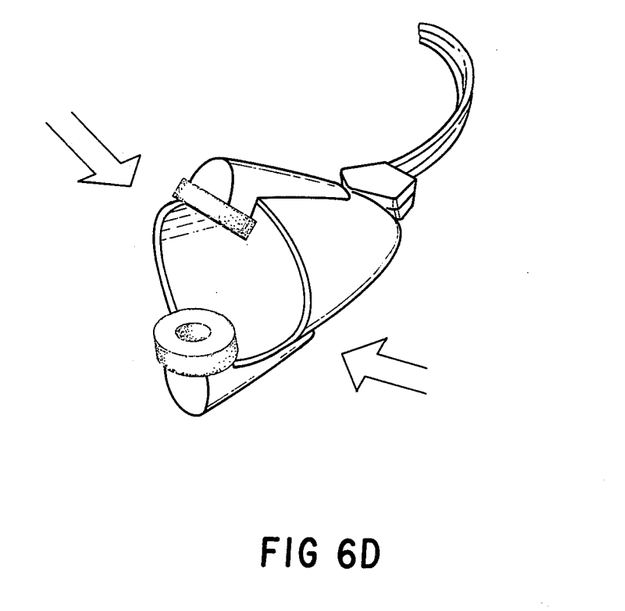

The relationship between illumination and photoconductive resistance is given by an equation of the form:

$$R = AI^k$$

where $R$ = photoconductive resistance
$I$ = illumination
$A$ and $k$ are constants and are dependent upon material To fully capitalized on the benefits of the logging operation, a unique probe had to be developed which would work equally well on fingers and toes as well as on the pinna of an ear. Historically, a transillumination has been used on ears whereas reflectance has been used on fingers and toes. The latter technique has shown considerable variability associated with application pressure and thus its usefulness, even with the logging operation, would be questioned. FIGS. 6A–D shows an optical probe that allows for equal usefulness on an ear, or finger and can very easily be applied to either simply by squeezing the sides of the "clamshell" as shown in FIG. 6C. In all cases, the application pressure, applied to either ear or finger, is not sufficient to squeeze the blood vessels and change the measurement.

Figure 8:
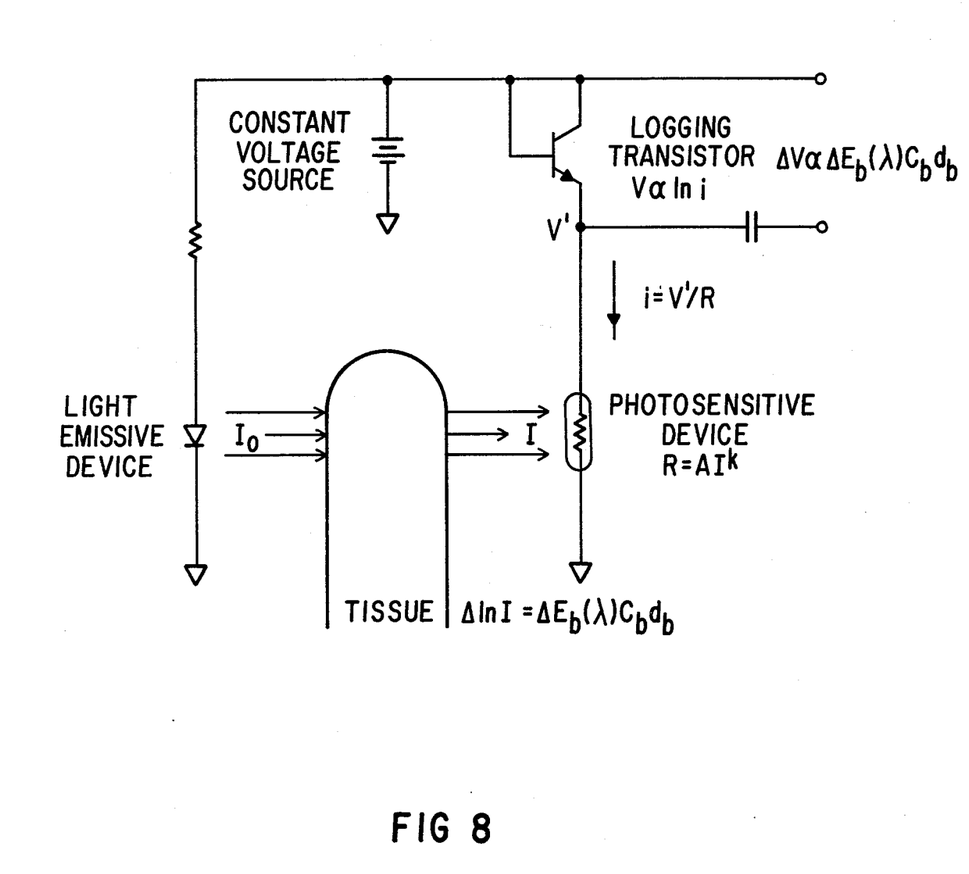
FIG. 8 is a simplified schematic diagram of the operation of the input and logging circuitry of the preferred embodiment.

Although the slope of the response characteristic in FIG. 11 is not perfectly constant, its deviation is small. That is, the changes in slope — from a thin white ear to a thick black ear to the tip of a finger — are small. Similarly, light history and temperature drift simply shift the operating point along the constant slope line. Thus, regardless of light history, temperature or sample transmission, the constants of the equation relating photoconductive resistance to illumination are changing but by a small percentage. This then, shows that logging provides for linearity, eliminates temperature and light history stability problems, and allows for reliable perfusion measurements on any tissue regardless of color or thickness. FIG. 8 shows a light emissive device emitting illumination, $I_o$, through tissue having pulsatile blood flow. If a constant voltage, $V$, is applied to the photoconductive resistance, $R = AI^k$, the current, $i$, is given by: $i = V/R$. Logging this current yields:

$$\ln i = \ln V - \ln R$$
$$= \ln V - \ln (AI^k)$$
$$= \ln V - \ln A - k \ln I$$

The time varying components of this equation are given by:

$$\frac{d}{dt} \ln i = \frac{d}{dt} \ln V - \frac{d}{dt} \ln A - \frac{d}{dt} k \ln I$$

or:

$$\Delta \ln i = -k \Delta \ln I$$

Earlier, however, it was shown, in the absence of field motion, the changes in the log of the transmitted light to be directly proportional to the changes in the blood thickness-concentration product. Therefore:

$$\Delta \ln i = k \Delta E_b(\lambda) D_b d_b$$

This equation shows that the only system determined variable is, $k$, which is a function of the slope of the photoconductive cell. By spectifying limits on the slope, instrument to instrument differences may be properly controlled. As the slope changes but by a small percentage under various illuminations, the historical problems of linearity and stability are solved.

Because a pn semiconductor junction exhibits a repeatable logarithmic relationship between current and voltage, it can be exploited to perform the needed logging operation. Since the diode connected transistor conducts the current from the photoconductive cell, and as the voltage drop across that junction approximates the log of that current, the changes in this voltage correspond to the changes in blood volume.

Figure 3:
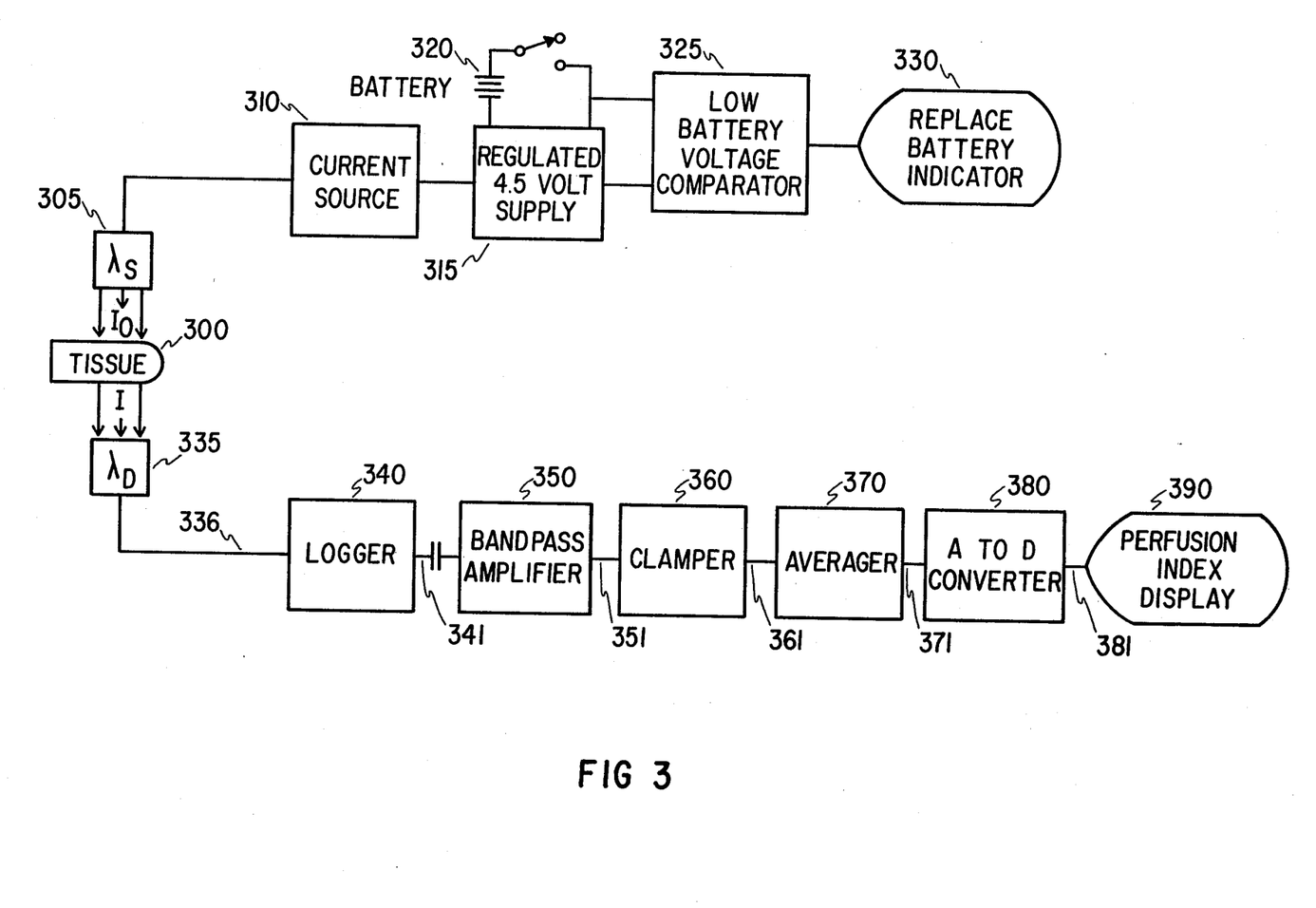
FIG. 3 shows a block diagram of the perfusion meter of the preferred embodiment.

In FIG. 3 there is shown a block diagram of the perfusion indicator in accordance with the preferred embodiment. A light source 305 is driven by a current source 310. The emitted light, Io, produced by light source 305 is directed towards tissue 300; the transmitted light, I, falls on photo-responsive device 335. A signal on a line 336 is produced by photo responsive device 335 in response to said transmitted light.

A logging circuit 340 produces an output signal on a line 341 which bears a logarithmic relationship to the signal received on line 336. The signal on line 341 is capacitively coupled to a bandpass amplifier 350. The passband of amplifier 350 is approximately 0.5–11 Hz, this being the frequency band of interest with respect to blood flow.

Figure 4:
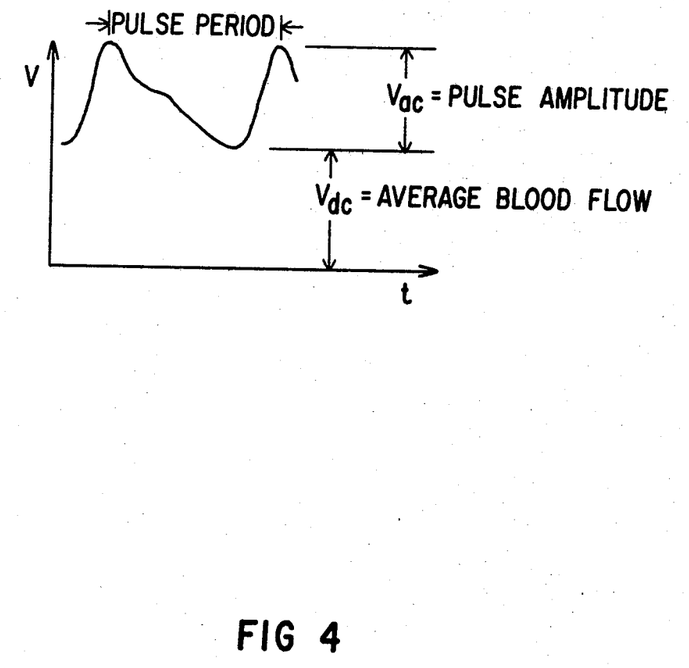
FIG. 4 shows the waveform of the signal obtained from the Averager circuit of the preferred embodiment.

An amplified pulse signal is produced on line 351 and coupled to a clamping circuit 360 which clamps the most negative portion of the pulse signal at zero volts. This produces a ground referenced waveform on line 361 which is then averaged by an averager circuit 370. The averager output signal on a line 371 has a DC voltage component (time integration of volume pulse) that is proportional to the average blood flow, effectively the volume pulse amplitude-heart rate product, and an AC voltage component that is proportional to the pulse amplitude. This waveform is shown in FIG. 4.

The signal on line 371 is input to analog to digital converter 380 which simultaneously produces a 7 level analog staircase voltage and decoding for a 7 bit digital response. The average waveform is constantly compared with the staircase voltage and if the comparison is met, a corresponding element in the perfusion index display is lit. Thus, a simple, inexpensive A to D conversion with built-in display is provided by this circuit.

The seven elements of the perfusion indicator display 390 are constantly strobed producing a bar graph type of display in response to the signal on a line 371. This bar graph display provides an indication called the perfusion index which is a measure of the pulsatile blood flow within the body tissue. Also, as mentioned above, this reading can be interpreted to indicate the possible error in an oximeter reading.

Figure 5:
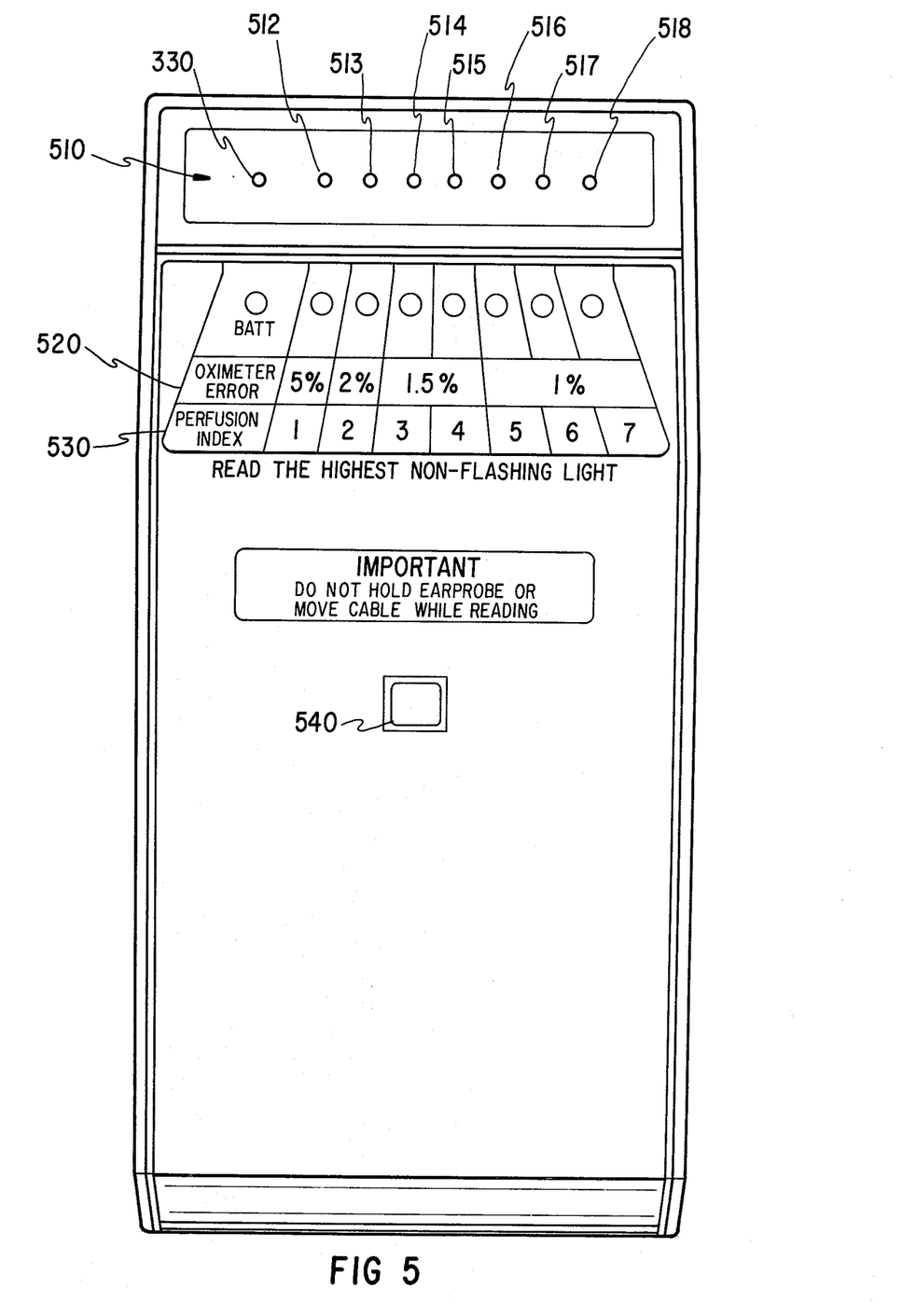
FIG. 5 is an illustration of the portable case and perfusion index display of the preferred embodiment.

Referring to FIG. 5, there are shown indicators 510 which are energized in response to the blood flow rate within the tissue under test. These indications may be interpreted per legend 520 as indicating the probable oximeter error or correction factor. These indications may also be interpreted using legend 530 as a direct measurement of the perfusion, i.e., the blood flow rate.

The representation provided by indicators 510 may be interpreted as a bar graph display. The illuminated length of the bar graph, starting at the leftmost indicator and continuing to the rightmost illuminated indicator, represents the average blood flow rate. The pulse rate is indicated by the flashing of the rightmost indicators. The strength of the pulse is indicated by the number of flashing indicators; more indicators flash on and off in sequence as the pulse strength increases.

Measurements may be made after stimulating the ear or other body tissue to produce the maximum blood flow. This is done by brisk rubbing and/or gentle heat. The plethysmograph is then placed over the pinna of the ear or other body surface and the interconnecting cord between the plethysmograph and the portable case 510 is draped to minimize interference from motion artifacts. A key 540 in the center of the indicator case is depressed and held. In less than ten seconds the bar graph display 510 settles to a reading which is a measure of the pulsatile blood flow rate within the ear or other tissue.

Figure 7A:
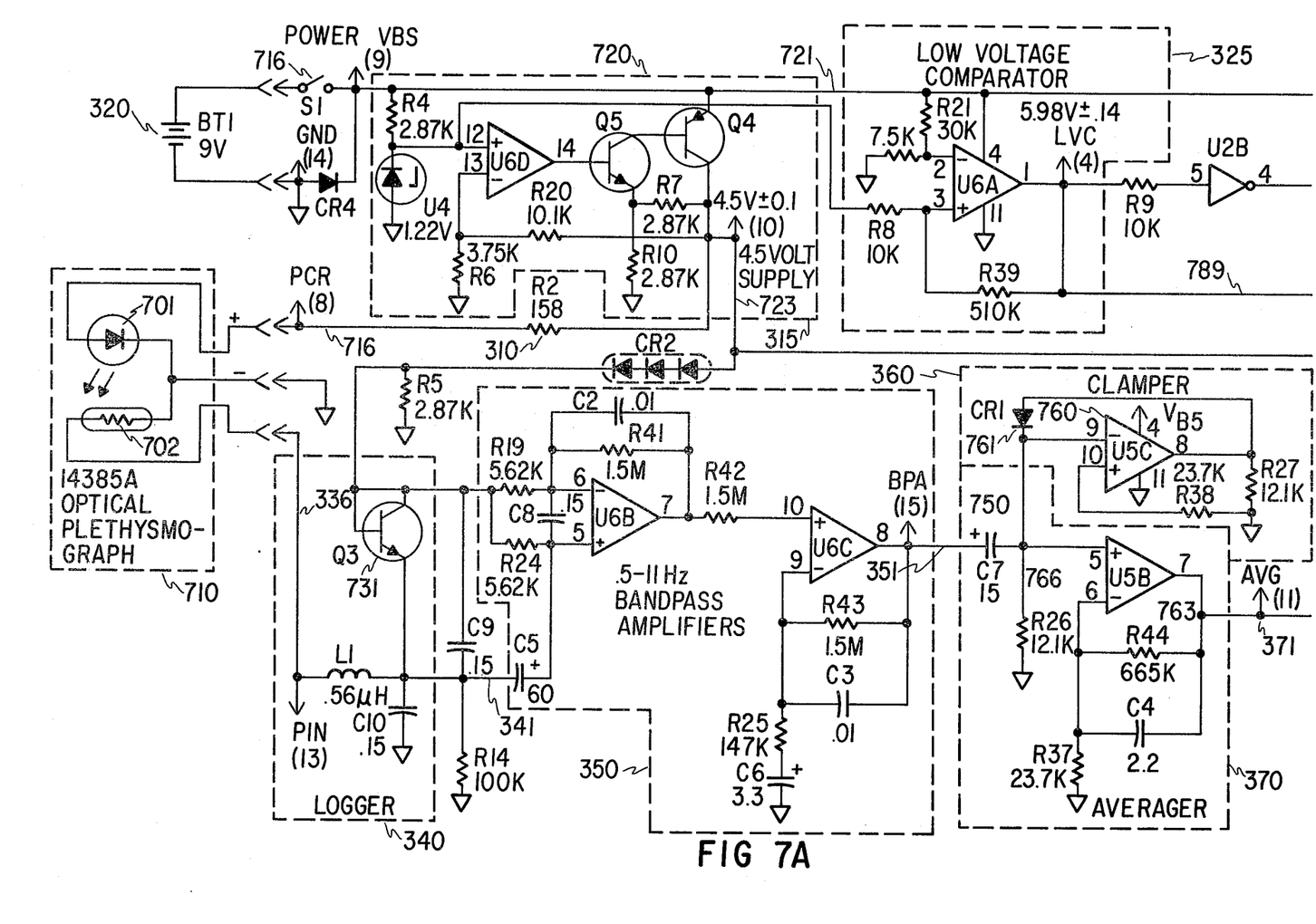
FIGS. 7A and 7B, taken together, are a schematic diagram of the circuitry of the preferred embodiment.
Figure 7B:
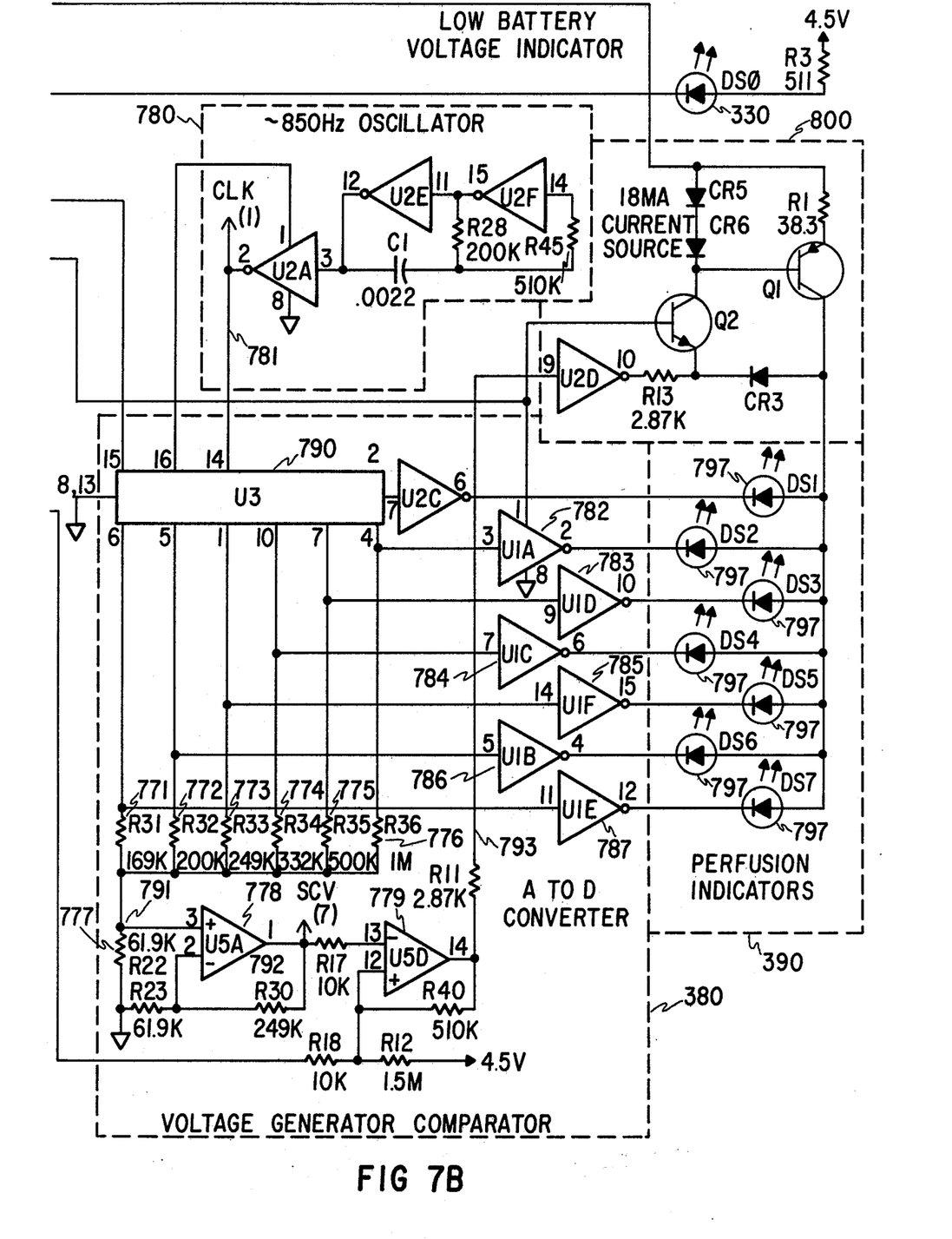

In FIG. 7 there is shown a schematic diagram of the circuitry of the preferred embodiment. A battery 320 is coupled through a power switch 716 to a power supply regulator circuit 720 which supplies 1-20 milliamps of current at 4.5 volts on line 723. Whenever the power is on, low voltage comparator circuit 325 continuously monitors the battery voltage 320 and automatically turns off the perfusion index display 390 and illuminates low battery voltage indicator 330 if the battery voltage is below a preset limit.

A current source is provided by circuit 720 and resistor 310. The current provided on a line 716 is used to drive the LED light source 701 within ear probe 710. Current is supplied to a photoconductive device 702 within an ear probe 710 by logging circuit 730.

Transistor 731 is connected to operate as a diode. The logarithmic properties of the PN semiconductor junction, as mentioned above, between current and voltage is exploited to perform the logging function. As shown earlier, the changes in this junction voltage correspond to the changes in blood volume. Inductor L1 and capacitor C10 form and L-C high frequency filter which helps eliminate unwanted interference. Capacitors C8 and C9 further reduce any high frequency interference.

The output from logger circuit 730 is capacitively coupled via capacitor 733, to low pass amplifier circuit 350. The combination of amplifiers within this circuit forms the 0.5-11 Hz bandpass amplifier and has a net gain of about 3,000, i.e., 70 DB, within the passband.

The output from amplifier circuit 350 is capacitively coupled by capacitor 750 to averager circuit 370. Circuit 370 acts as an averager while circuit 360 is the clamping circuit. The clamping function is performed by amplifier 760 which has negative feedback through diode 761 to prevent the inputs of amplifier 760 and 763 from ever going negative. Thus, the entire pulse waveform is positive with reference to ground except for the input offset voltage of amplifier 760.

This ground referenced waveform on line 766 is then averaged by circuit 370. The output signal on line 371 has an amplified average, i.e., a DC voltage proportional to the average blood flow, and a non-amplified pulse waveform, i.e., an AC voltage waveform proportional to pulse strength. Oscillator 780, shown in FIG. 7B provides the signal on a line 781 to decade counter and decoder 790 within analog to digital converter circuit 380. Whenever the reset line, pin 15, of decade counter and decoder 790 is low, the decade counter is counting and one of the ten outputs will be decoded and an output signal therefrom will remain high for one clock period. Seven of these output signals are used to generate a staircase voltage on a line 791. Also, these seven outputs from decade counter and decoder 790 are used to strobe the LED display devices 797. Note that whenever the battery voltage is sufficiently low to trigger low voltage comparator circuits 325, the enable signal on line 789 is removed and thus staircase voltage generator 778 and indicator displays 797 are disabled.

Resistors 771, 772, 773, 774, 775, 776, and 777 are chosen to give a staircase voltage at the input terminal of amplifier 778. The output on line 792 from amplifier 778 is a staircase waveform comprising seven voltage values varying from 0 volts DC to 3.6 volts DC in 0.6 volt increments. Each of the voltages appears for one full clock cycle and reoccurs every ten clock cycles. Amplifier 779 completes the analog to digital conversion by continuously comparing the output from averager circuit 370 with the various steps of voltage.

If the output signal on line 371 exceeds the staircase voltage, the output on line 792 from amplifier 779 goes high and activates the current source 800 for the perfusion indicator display 797. Thus, whenever this condition is met a current source 800 is activated and the appropriate buffer gate, i.e., gates 782, 783, 784, 785, 786 and 787, are turned on and current is passed through one of the LED indicators in display 797. Note that indicator display 797 will provide two separate pieces of information. One is that the number of LEDs which are lit in display 797 will correspond to the DC level of the signal output by averagers circuit 370. Also, the number of indicators in display 797 which are flashing on and off will indicate the strength of the pulse through the tissue under test, the more lights that are flashing on and off the stronger the pulse rate.

We claim:
1. Apparatus for measurement of pulsatile blood flow rate through a tissue area, said apparatus comprising:
   input means having a light-emissive device and a photosensitive device for providing a first electrical signal in response to pulsatile variations in the quantity of light from said light-emissive device which passes through said tissue and which falls on said photosensitive device;
   second means coupled to the input means for providing a second electrical signal which has a logarithmic relationship to said first electrical signal;
   display means coupled to the second means for providing a visual indication in response to said second electrical signal, said display means including a plurality of indicators, a corresponding legend, and means for activating said indicators in response to said second electrical signal;

said legend comprising a first set of symbolic markings approximately representing an average pulsatile blood flow rate; and said legend further comprising a second set of symbolic markings representing the approximate error to be expected in an oximeter reading at the corresponding blood flow rate.

2. Apparatus as in claim 1 wherein the number of activated indicators provides an indication of the average pulsatile blood flow rate, and at least one indicator flashes on and off at a rate corresponding to the pulse rate.

3. Apparatus as in claim 2 wherein the number of flashing indicators represents the strength of the pulse rate.

* * * * *

UNITED STATES PATENT AND TRADEMARK OFFICE
CERTIFICATE OF CORRECTION

PATENT NO. : 4,109,643
DATED : August 29, 1978
INVENTOR(S) : Albert K. Bond, Edwin B. Merrick, Larry J. Neilsen It is certified that error appears in the above-identified patent and that said Letters Patent are hereby corrected as shown below:

Column 4, the equation at line 25 should appear as follows:

$$\frac{d}{dt}A(\ ) = -\frac{d}{dt}\ln(I/I_o) = \frac{d}{dt}E_1(\lambda)C_1d_1 + \frac{d}{dt}E_2(\lambda)C_2d_2 + \ldots + \frac{d}{dt}E_N(\lambda)C_Nd_N$$

Signed and Sealed this

Sixth Day of March 1979

[SEAL]

Attest:

RUTH C. MASON
Attesting Officer

DONALD W. BANNER
Commissioner of Patents and Trademarks